(12) United States Patent
Higazi

(10) Patent No.: US 6,861,054 B2
(45) Date of Patent: Mar. 1, 2005

(54) SUPAR STIMULATING ACTIVITY OF TCUPA-MEDIATED FIBRINOLYSIS AND DIFFERENT USES THEREOF

(76) Inventor: Abd. Al-Roof Higazi, Neve Shalom, 99761 D.N. Shimshon (IL)

( * ) Notice: Subject to any disclaimer, the term of this patent is extended or adjusted under 35 U.S.C. 154(b) by 0 days.

(21) Appl. No.: 09/968,752

(22) Filed: Oct. 2, 2001

(65) Prior Publication Data

US 2002/0022025 A1 Feb. 21, 2002

Related U.S. Application Data

(63) Continuation of application No. PCT/IL00/00208, filed on Apr. 3, 2000, now abandoned.

(30) Foreign Application Priority Data

Apr. 5, 1999 (IL) ................................... 129332

(51) Int. Cl.[7] .......................... A61K 38/48; C12N 9/64; C12N 9/50
(52) U.S. Cl. ..................... 424/94.64; 435/226; 435/219
(58) Field of Search .......................... 424/94.63, 94.64; 514/12; 530/350; 435/226, 219

(56) References Cited

U.S. PATENT DOCUMENTS

| | | | | |
|---|---|---|---|---|
| 5,455,044 A | | 10/1995 | Kim et al. ................... | 424/450 |
| 5,558,852 A | | 9/1996 | Bigner et al. ............... | 424/1.29 |
| 5,891,664 A | * | 4/1999 | Danøet al. ................... | 435/69.1 |
| 6,462,170 B1 | * | 10/2002 | Blasi et al. .................. | 530/300 |

FOREIGN PATENT DOCUMENTS

WO   WO 98/25641   6/1998

OTHER PUBLICATIONS

Higazi et al., "Lysis of Plasma Clots by Urokinase–Soluble Urokinase Receptor Complexes" (Sep. 15, 1998) Blood, 92(6), 2075–2083.*
Higazi et al., "Single–Chain Urokinase–Type Plasminogen Activator Bound to its Receptor is Relatively Resistant to Plasminogen Activator Inhibitor Type 1" (1996) Blood, 87(9), 3545–3549.*
Higazi et al., "Interaction of Single–Chain Urokinase with its Receptor Induces the Appearance and Disappearance of Binding Epitopes within the Resultant Complex for Other Cell Surface Proteins" (1996) Blood, 88(2), 542–551.*
Pannell, R. & Gurewich V., Blood, 69: 22–26 (1987).
Kasai, S. et al. J. Biol. Chem. 260: 12382–12389 (1985).
Lindahl, T. L. et al. Biochem. J. 265: 109–113 (1990).
Ellis, V. et al., J. Biol. Chem. 265: 9904–9908 (1990).
Nykjaer, A. et al. J. Biol. Chem. 269: 25668–25676 (1994).
Deutsch, D. & Mertz E.T., Science 170: 1095–1096 (1970).
Higazi, AA–R et al., J. Biol. Chem. 270: 9472–9477 (1995).
Higazi, AA–R et al., Biochem. J. 300: 251–255 (1994).

* cited by examiner

*Primary Examiner*—Jon P. Weber
(74) *Attorney, Agent, or Firm*—Rashida A. Kamali

(57) ABSTRACT

The present invention relates to a complex (tcuPA/suPAR) of the two chain urokinase plasminogen activator (tcuPA) with the soluble urokinase plasminogen activator (suPAR), to pharmaceutical compositions comprising this complex and to different uses of the compositions in the treatment and/or prevention of thrombotic events, particularly those associated with the formation of fibrin clots. In the complex (tcuPA/suPAR), the suPAR stimulates fibrinolytic activity mediated by tcuPA under physiological conditions. The complex acts preferably on freshly-formed clots and is specific to such clots.

7 Claims, 3 Drawing Sheets

(1) (2) (3) (4)

SUPAR STIMULATING ACTIVITY OF TCUPA-MEDIATED FIBRINOLYSIS AND DIFFERENT USES THEREOF

This application is a continuation of International Application PCT/IL00/00208, with an international filing date of Apr. 3, 2000, now abandoned, which claims priority from Israeli Application Serial No. IL 129332, filed Apr. 5, 1999.

FIELD OF THE INVENTION

The present invention relates a complex of the two chain urokinase plasminogen activator (tcuPA) with the soluble urokinase plasminogen activator receptor (suPAR) or with fragments thereof, pharmaceutical compositions comprising said complex as active ingredient and to the different uses of said compositions in the treatment and/or prevention of thrombotic events.

BACKGROUND OF THE INVENTION

Acute myocardial infraction, stroke, pulmonary emboli and other thrombotic events are the major causes of death in developed countries. Tremendous efforts have been made to develop drugs that can prevent or improve acute thromboembolic events. Amongst these drugs are thrombolytic agents that are used widely in the acute setting. However, the utility of currently available thrombolytics is limited by the high-risk of bleeding which accompanies their use. This danger results from the high doses that are required to lyse clots, which cause plasmin to accumulate in the circulation, resulting in systemic fibrinolysis and fibrinogenolysis. Intracranial hemorrhage occurs in approximately 1% of patients receiving thrombolytic agents and other major hemorrhagic complications occur with a comparable incidence. These side effects limit the use of thrombolytic agents to the relief of ischemia only in the most severe cases.

Other limitations of available thrombolytic treatment include the length of time required for clot lysis to be achieved and blood vessel potency to be reestablished. In addition, available thrombolytic agents do not distinguish between newly formed clots, responsible for the acute event, and "aged" clots which may serve a physiological purpose.

Based upon these considerations, it would be advantageous to develop a thrombolytic agent that would act only in the presence of fibrin, would have a rapid onset of action and be specific for recently formed clots. These properties would make it possible to lyse clots more rapidly, with lower concentrations of the agent, thereby reducing the prevalence of systemic bleeding. The ability of such an agent to distinguish between recently formed and older clots would reduce the probability of further bleeding.

Plaminogen activators are widely used in the treatment of thromboembolic diseases. One of these activators is urokinase plasminogen activator (uPA), known to be synthesized as a proenzyme consisting of a single-chain protein (scuPA) [Pannell, R. & Gurewich V. Blood 69:22–28 (1987)] and to be involved in several important biological processes including angiogenesis, wound healing, inflammation, ovulation and placental development, atherosclerosis, aneurysm and neointima formation and the formation of tumor metastases.

Limited proteolysis of scuPA results in the formation of two chains (tcuPA), considered to be the active form of the enzyme [Kasai, S. et al. J. Biol. Chem. 260:12382–12389 (1985)]. One of the most important regulators of uPA is the plasminogen activator inhibitor-1 (PAI-1). This regulator interacts with tcuPA in a very rapid two-step reaction, leading to the formation of an inactive, SDS-stable 1/1 complex [Lindahl, T. L. et al. Biochem. J. 265:109–113 (1990)]. The binding of tcuPA to uPAR only slightly reduces the susceptibility of tcuPA to the inhibitory effect of PAI-1 [Ellis, V. et al. J. Biol. Chem. 265:9904–9908 (1990)].

Over the last years, the inventors have been engaged in developing and characterizing novel plasminogen activators that fulfill the above specified criteria.

It has now been surprisingly found that soluble human urokinase receptor (suPAR) stimulates the activity of the commonly used thrombolytic agent tcuPA, under specific conditions in vitro. As will be shown in the following Examples, the activity of the tcuPA/suPAR complex which is formed between the said two components, is fibrin-dependent and requires the presence of specific plasma or serum components(s).

Further, as will also be shown in the following Examples, under in vivo conditions, suPAR, by complexing with tcuPA, significantly enhanced lysis of pulmonary emboli, compared to lysis by tcuPA in the absence of the receptor.

SUMMARY OF THE INVENTION

The present invention relates to a complex of tcuPA with suPAR, or fragment/s of said suPAR (said complex also referred to herein as tcuPA/suPAR), in which the suPAR, or said fragment/s thereof, stimulates fibrinolytic activity mediated by tcuPA under physiological conditions.

The complex according to the invention acts preferably on freshly-formed clots and therefore is specific thereto.

In a second aspect, the invention relates to a pharmaceutical composition comprising as active ingredient a therapeutically effective amount of the suPAR/tcuPA complex of the invention. The compositions according to the invention may optionally further comprise pharmaceutically acceptable carriers, diluents, adjuvants and preserving agents.

In a preferred embodiment, the pharmaceutical compositions of the invention are for the treatment and/or prevention of thrombotic events associated with the formation of fibrin clots.

The invention is also concerned with the use of suPAR as a stimulator of the fibrinolytic activity of tcuPA, particularly for the treatment of thrombotic events.

DETAILED DESCRIPTION OF THE INVENTION

Figure 1:
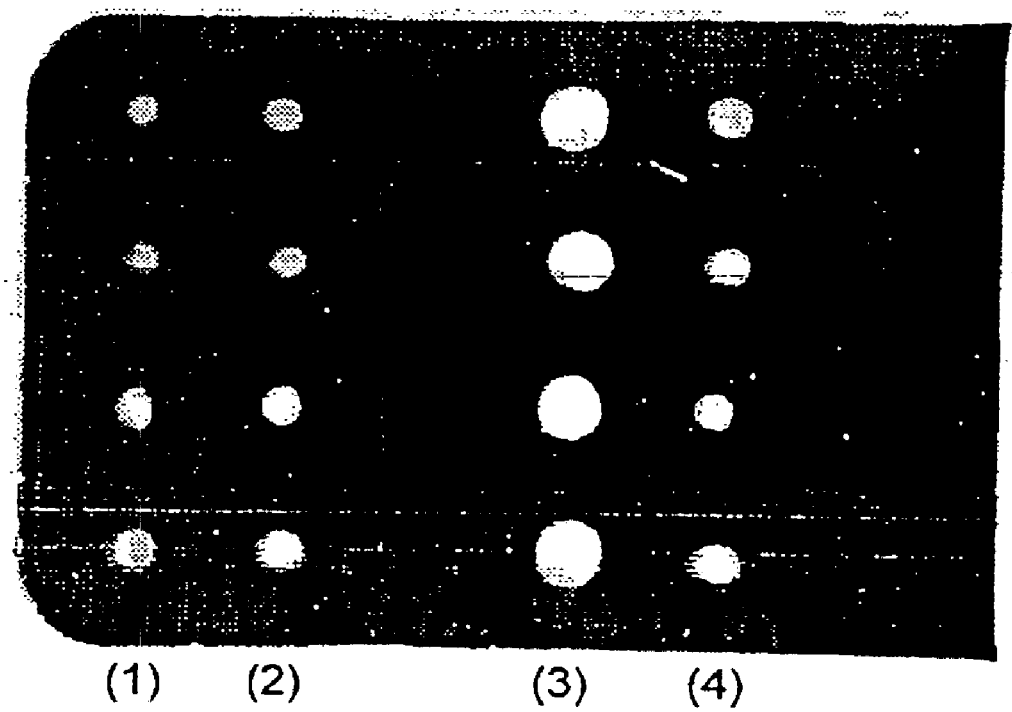
FIG. 1 Effect of suPAR on tcuPA-mediated clot lysis Lysis of clots prepared from human plasma. Clots were prepared by adding thrombin (0.4 NIH U/ml final concentration). TcuPA or equimolar concentrations of suPAR and tcuPA (tcuPA/suPAR) were added for 2–3 hrs, at 37° C. Lanes 1 and 4 show the fibrinolytic activity mediated by tcuPA alone. Lane 2 shows the fibrinolytic activity mediated by tcuPA/suPAR at a concentration ratio of 1:1. Lane 3 shows the activity mediated by tcuPA/suPAR at a concentration ratio of 1:10. The sizes of the lytic areas generated by tcuPA/suPAR are observed.

The present invention relates to a complex of tcuPA with suPAR or with fragments of suPAR, which complex is believed to directly or indirectly induce fibrinolysis of plasma-derived clots, by suPAR stimulation of the fibrinolytic activity mediated by tcuPA. In particular, the fibrinolytic activity ascribed to suPAR/tcuPA is essentially specific to fresh fibrin clots.

It should be clear that the term suPAR refers to the receptor per se, or to functional fragments or derivatives thereof. By the term functional fragment or derivative is meant any fragment or derivative of suPAR which exhibits the biological activity of suPAR, particularly the stimulation of fibrinolytic activity mediated by tcuPA.

The terms 'fibrin clots' or 'plasma-derived clots' mean clots formed by the conversion of fibrinogen to fibrin, whereby red blood cells and other formed elements are entrapped within the coagulated plasma. The enzyme catalyzing this conversion is known to be thrombin, which is formed in shed blood and converts fibrinogen into fibrin, thereby producing fibrin clots by a hydrolyzing action.

The fibrinolytic activity of the scuPA/suPAR complex, in vivo, under physiological conditions, as compared to the activity of tcuPA alone or in combination with suPAR, was described in WO98/25641. The results presented therein clearly show that suPAR has only marginal effect on tcuPA-mediated fibrinolysis, when applied to a fibrin clot at a 1:1 stoichiometry.

However, the inventors have now found that despite the consensus that pro-uPA's, e.g. scuPA or tcuPA, bind to their receptor, uPAR, in a 1:1 ratio [A. Nykjaer et al J. Biol. Chem. 269(41):25668–25676 (1994)], when employing an excess amount of suPAR (for example, suPAR/tcuPA 10:1), the receptor or at least a functional fragment thereof, has an unexpected stimulatory effect on tcuPA-mediated fibrinolysis. This novel finding may indicate a different and novel mechanism of action of tcuPA, being activated only in the presence of an excess amount of suPAR.

In a second aspect, the invention concerns a pharmaceutical composition comprising as active ingredient a therapeutically effective amount of the tcuPA/suPAR complex of the invention.

The 'therapeutically effective amount', for purposes herein, is determined by such considerations as are known in the art. The amount must be effective to achieve improvement including but not limited to improved survival rate or more rapid recovery, or improvement or elimination of symptoms and other indicators as are selected as appropriate measures by those skilled in the art. The doses may be single doses or multiple doses over a period of several days, but single doses are preferred.

The tcuPA/suPAR complex or the pharmaceutical composition of the invention can be administered in various ways and may comprise, in addition to the active ingredient, pharmaceutically acceptable carriers, diluents, adjuvants, preserving agents and vehicles. According to one embodiment, the pharmaceutical composition of the invention is in a dosage unit form.

The pharmaceutical compositions can be administered subcutaneously or parenterally including intravenous, intraarterial, intramuscular, and intraperitoneal administration, as well as intrathecal techniques. Implants of the pharmaceutical preparations may also be useful. The pharmaceutically acceptable carriers, diluents, adjuvants and vehicles as well as implant carriers generally refer to inert, non-toxic solid or liquid fillers, diluents, or encapsulating material not reacting with the active ingredients of the invention.

When administering the complex or the pharmaceutical composition of the invention parenterally, it will generally be formulated in a unit dosage injectable form (solution, suspension, emulsion). The pharmaceutical formulations suitable for injection include sterile aqueous solutions and sterile powders for reconstitution into sterile injectable solutions. The carrier can be any physiologically acceptable suitable carrier, for example, water, or aqueous buffer solutions.

Proper fluidity can be maintained, for example, by the use of a coating such as lecithin, by the maintenance of the required particle size in the case of dispersion and by the use of surfactants. Non-aqueous vehicles such as cottonseed oil, sesame oil, olive oil, soybean oil, corn oil, sunflower oil or peanut oil and esters, such as isopropyl myristate, may also be used as solvent systems for compound compositions.

In addition, various additives which enhance the stability, sterility and isotonicity of the compositions, including antimicrobial preservatives, antioxidants, chelating agents and buffers can be added. Prevention of the action of microorganisms can be ensured by various antibacterial and antifungal agents, for example, parabens, chlorobutanol, phenol, sorbic acid and the like. In many cases it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, any vehicle, diluent, or additive used would have to be compatible with the compositions.

Sterile injectable solutions can be prepared by incorporating the compositions utilized in practicing the present invention in the required amount of the appropriate solvent with various of the other ingredients, as desired.

Nonetheless, the composition disclosed herein in detail can be administered orally to the patient. Conventional forms such as administering the composition as tablets, suspensions, solutions, emulsions, capsules, powders, syrups and the like are usable. Known techniques which deliver it orally or intravenously and retain the biological activity are preferred.

For delivery within the CNS intrathecal delivery can be used with for example an Ommaya reservoir. U.S. Pat. No. 5,455,044 provides for use of a dispersion system for CNS delivery or see U.S. Pat. No. 5,558,852 for a discussion of CNS delivery. In addition, pharmacological formulations that cross the blood brain barrier can be administered. Such formulations can take advantage of methods now available to produce chimeric structures in which the complex of the invention, alone of in combination with human IgG or said IgG-derived peptide/s are coupled to a brain transport vector thus allowing transportation across the barrier. Further, in appropriate cases blood brain barrier disruption can be utilized.

The pharmaceutical composition according to the invention is intended for the treatment of thrombotic events associated with formation of fibrin clots. The term thrombotic event is well known to the man of the art, and may include inter alia, acute myocardial infraction, stroke, pulmonary emboli, cerebro-vascular events, disseminated intravascular coagulation (DIC), or deep vain thrombosis, but by no means should be limited thereto.

Evidently, any other disorder associated with the damaging formation of fibrin clots may also be treated or prevented by use of suPAR or the complex of the present invention.

In a further aspect, the invention relates to the use of suPAR as a stimulating agent for the fibrinolytic activity of tcuPA.

Further, the invention relates to the use of a complex of tcuPA/suPAR, in the preparation of a pharmaceutical composition, the composition being particularly for the treatment of thrombotic events associated with the formation of fibrin clots. As indicated above, the thrombotic events against which suPAR or suPAR/tcuPA may be used may include acute myocardial infraction, stroke, pulmonary emboli, cerebro-vascular events or deep vain thrombosis.

Yet further, the invention relates to a method for treating and/or preventing a thromboembolic disorder associated with the formation of fibrin clots in a patient in need of such treatment by administering to said patient a therapeutically effective amount of scPAR or of a complex comprising suPAR/tcuPA. The method according to the invention may be utilized for the treatment of acute myocardial infraction, stroke, pulmonary emboli, cerebro-vascular events or deep vain thrombosis, however, should not be limited to these disorders.

The invention will now be described in more detail on hand of the following Examples, which are illustrative only and do not limit the scope of the invention, which is defined by the appended claims.

EXAMPLES

Materials and Methods

SuPAR was a gift of Dr. J. Henkin and Dr. A. Mazar, Abbott Laboratories, Abbott Park, Ill. Human fibrinogen and human thrombin were purchased from Sigma, St. Louis, Mo. TcuPA was purchased from American Diagnostics, Greenwich, Conn. Plasminogen was prepared as described by Deutsch and Mertz [Deutsch D. & Mertz E. T., Science 170:1095–1096 (1970)]. Plasma was obtained from the Hadassah Hospital blood bank. Blood used to obtain plasma was drawn from healthy volunteers. Blood (450 ml) was collected in bags produced by Travenol Laboratories, Ashdod, Israel, containing 63 ml of CPD solution (containing 1.66 g sodium citrate (hydrous), 61 g dextrose, 206 mg citric acid and 140 mg moon basic sodium phosphate). Plasma was separated by centrifugation.

Radiolabeled Fibrinogen

Plasminogen-depleted human fibrinogen (Fib 1-1340, American Diagnostics, Greenwich, Conn.) was trace radio-labeled with $^{125}$I (NEN Life Sciences). $^{125}$I-fibrinogen (~40×10$^6$ cpm) was added to 1 ml unlabeled fibrinogen (35 mg/ml) before the micro-emboli were prepared.

Preparation of Micro-emboli

Human blood from healthy volunteers was collected in citrate (final concentration 0.32%). Plasma was isolated from the human blood by centrifugation at 1200 xg.

Clots were formed by first adding 1 ml trace-labeled human $^{125}$I-fibrinogen to 2.5 ml plasma. CaCl$_2$ and human thrombin (Sigma) were then added at a final concentration of 20 mM and 0.2 U/ml, respectively, followed by incubation for 1 hr at room temperature and further incubated overnight at 4° C. From this point all steps were performed at 4° C. The fibrin clots were decanted onto the lids of culture dishes, and then cut into small pieces and re-suspended in 2 ml of PBS buffer. The micro emboli were then suspended in 13 ml PBS buffer containing 3 mg/ml BSA. Immediately before injection, the preparations were sedimented for 5 min. in order to remove any larger aggregates which may have been formed. The supernatant was aliquoted into 0.2 ml doses for injection. Random aliquots of micro-emboli were selected to characterize the size distribution (characterized previously as 10–100 μm) using a Coulter Counter.

Mice uPA depleted mice (uPA-\-), on a 25% Swiss/75% C57 blank background, and littermate controls were kindly provided by Dr. P. Carmeliet (Leuven, Belgium). All mice weighed 20–30 g at the time of the study.

In vitro Experiments

Assessment of Fibrinolysis by Reduction in Clot Size

Human fibrinogen [Sigma, St. Louis Mo.] was reconstituted in phosphate buffered saline (PBS, pH 7.4) or in plasma to a concentration of 9 mg/ml, after which human thrombin was added (0.4 NIH U/ml) to form clots. The mixture was decanted onto culture dish lids and incubated for 60 min, at room temperature. After clot formation, aliquots of phosphate-buffered saline (PBS), pH 7.4, containing tcuPA (10 pmole in 10 μl PBS) was added to the surface of the clot in the presence of absence of 0–100 pmol suPAR. As a control, no tcuPA was added to several lids containing formed clots. The clots, in the presence or absence of suPAR, were then incubated for a further period of 2–3 hr, at 37° C., during which the appearance of digestion areas was observed. At that stage, the clots were washed several times with PBS and incubated overnight with 0.2% trypan blue. On the following day the clots were rinsed four times with PBS and photographed. The size of the lytic zones was calculated by the NIH image program (FIG. 1).

Assessment of Fibrinolysis by Measuring the Release of Radioactivity

Figure 2:
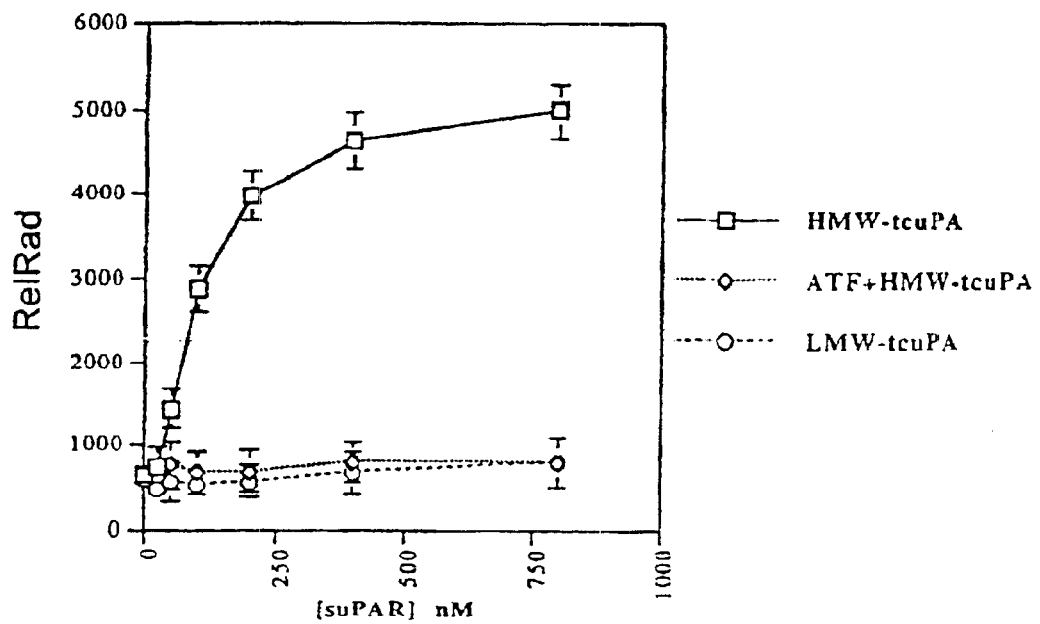
FIG. 2 suPAR stimulates tcuPA-mediated fibrinolysis Plasma clots were supplemented with. $^{125}$I-fibrin and incubated with plasminogen and tcuPA in the presence of the indicated concentrations of suPAR. The released radioactivity (RelRad) was determined after 1 hr., at 37° C. and the radioactivity released into the supernatant was measured. The mean ±SEM of three repeated experiments is shown. The concentration of HMW- or LMW-tcuPA was 25 nM. The values indicated are means of three experiments.

Human fibrinogen (American Diagnostics USA) was radiolabeled with $^{125}$I [Higazi, AA-R et al. J. Biol. Chem. 270:9472–9477 (1995)] and re-suspended in either PBS solution (pH 7.4) or in plasma at a fibrinogen concentration of 3 mg/ml. The final radioactivity of these preparations was ~30,000 cpm/ml. Clots were formed in 16 mm tissue culture wells (Costar, Cambridge, Mass.) by the addition of thrombin (0.4 NIH U/ml) to each well. The plasminogen activator (400 μl of HMW-tcuPA, 25 nM), was added directly to the center of each formed clot and after incubation for specific periods the wells were washed with PBS and the level of radioactivity released into the lavage solution was determined by a gamma counter. FIG. 2 illustrates the plasminogen activation by the complex suPAR/tcuPA after 1 hr of incubation at 37° C.

Fibrinolysis was also measured as previously described [Higazi, AA-R., et al. Biochem. J. 300:251–255 (1994)], by addition of 0.4 ml serum or PBS containing plasminogen activator, tcuPA (25 nM) in the presence or absence of suPAR (50 nM). The plates were incubated at 37° C. for various time periods in which aliquots of 25 μl were removed for counting the solubilized label in a gamma counter. Fibrinolytic activity was determined by following the release from the $^{125}$I-labeled fibrin clot of labeled soluble degradation products of fibrin and is illustrated in FIG. 3.

Results

Plasma derived clots were used to examine the effect of suPAR on the activity of tcuPA. The activity of tcuPA was substantially stimulated at molar concentrations of suPAR greater than 1:1 (FIGS. 1 and 2). This stimulation could be suppressed by amino terminal fragment of urokinase (ATF) (which competes with tcuPA for receptor binding). In the presence of LMW-tcuPA, lacking the receptor-binding determinant, no stimulation was observed (data not shown). Blocking of the interaction of tcuPA with suPAR by ATF, caused almost complete inhibition of the stimulatory effect of suPAR on tcuPA mediated fibrinolysis (FIGS. 1 and 2).

Figure 3:
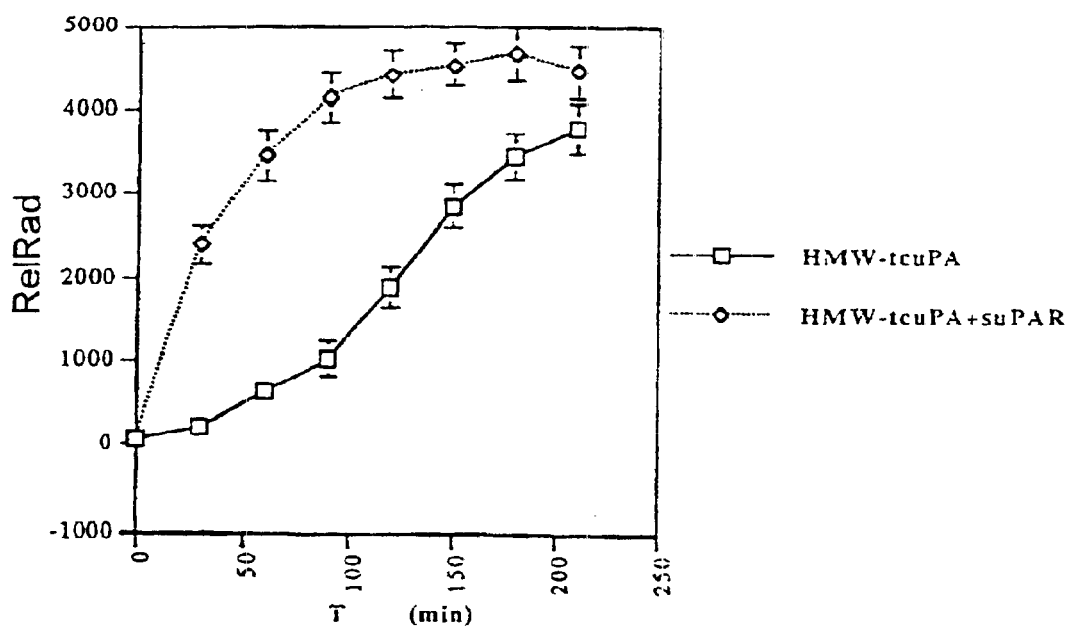
FIG. 3 The effect of suPAR on HMW-tcuPA mediated fibrinolysis HMW-tcuPA was incubated with freshly prepared clots, in the presence and absence of suPAR. The values indicated are means ±SEM of three repeated experiments. T designates time (in minutes).

FIG. 3 show that in the presence of tcuPA, suPAR-mediated cleavage rate of the plasma clots was faster and to a greater extent than do equimolar concentrations of tcuPA.

To exclude the possibility that the stimulatory effect of tcuPA was due to contaminating scuPA, SDS-PAGE was performed, which confirmed the absence of scuPA in the reaction mixture (data not shown).

When clots formed from purified fibrinogen were employed, no stimulation by suPAR-of tcuPA-mediated fibrinolysis was observed.

The data presented herein indicate that all of the components necessary for suPAR to stimulate the activity of tcuPA are present in freshly isolated serum. Nonetheless, the effect of serum was lost when kept overnight at 30° C., however, no loss of stimulatory activity was observed with plasma maintained under the same conditions, even for several days. These results suggest that the stimulatory factor(s) in serum underwent activation during storage. The differences between plasma and serum may indicate that after coagulation is initiated, the half-life of the stimulatory factor is limited. Further, these results indicate that freshly-formed clots will be lysed more efficiently than aged clots.

In vivo Experiments

The Effect of suPAR on the Ability of tcuPA to Cleave Plasma Clots in vivo

Figure 4:
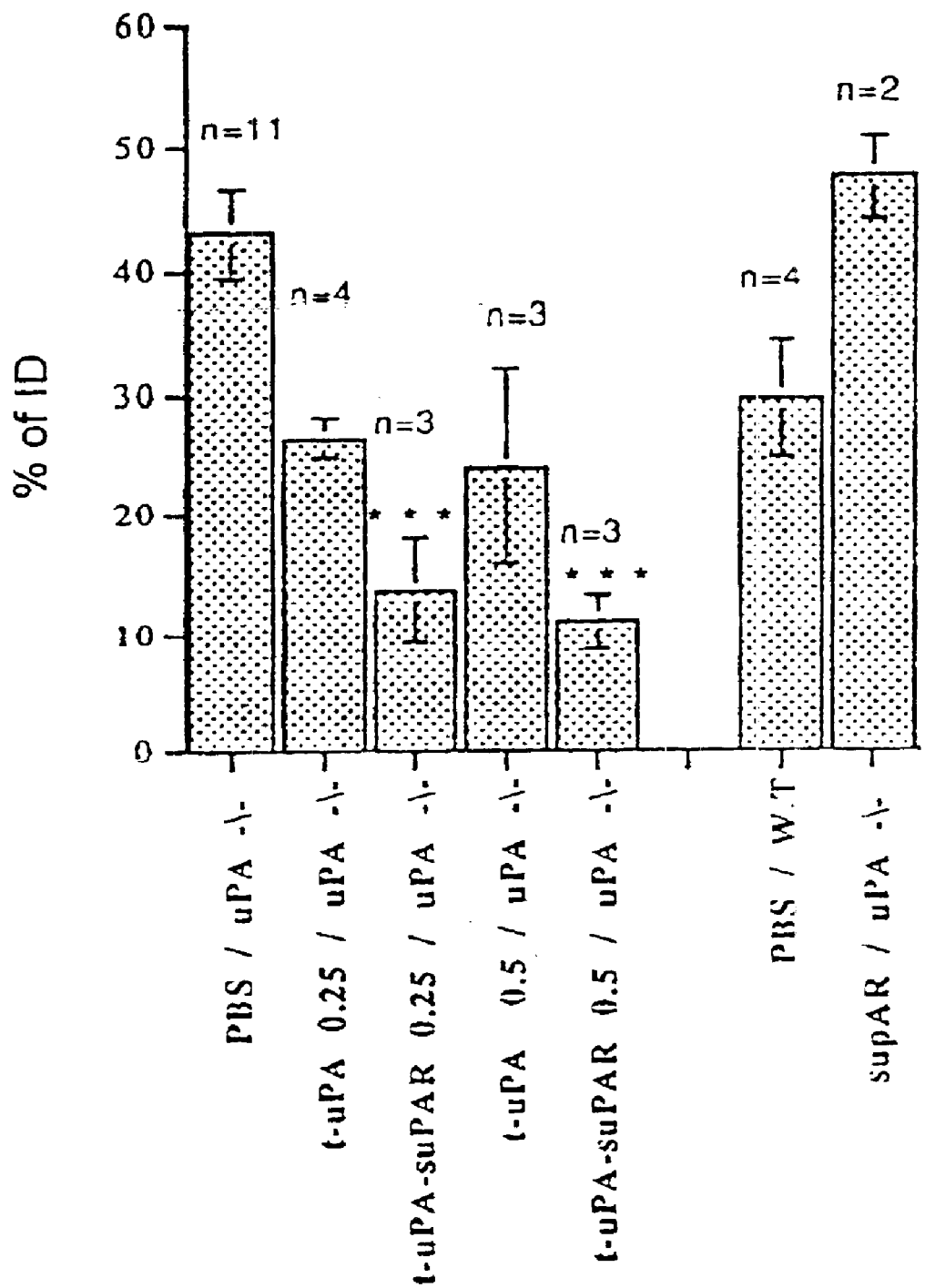
FIG. 4 suPAR stimulates tcuPA-mediated fibrinolysis in vivo uPA$^{-/-}$ mice (uPA-depleted mice) and their syngeneic wild type littermates received tcuPA, tcuPA/suPAR, suPAR or PBS, via continuous IV infusion. One hour after injection of $^{125}$I-microemboli, the radioactivity in the lungs was measured. The data is expressed as the difference between spontaneous clot lysis in wild type mice and the obtained in uPA$^{-/-}$ mice infused with PBS, tcuPA, tcuPA/suPAR or suPAR. The mean ±SEM of 2 experiments is presented. ID designates injected dose. For cases designated by ***, p=<0.001 compared to uPA$^{-/-}$ mice infused with PBS.

Radiolabeled micro-emboli were injected into the tail vein of mice and the plasminogen activator was injected into the jugular vein. The fibrinolytic activity of the various agents, i.e. tcuPA, tcuPA/suPAR or suPAR alone, was compared to a spontaneous clot lysis which served as a control, by measuring the rate in which radioactivity was cleared from the lungs of the mice. The results presented in FIG. 4 clearly indicate that while suPAR alone has no fibrinolytic activity, in the presence of tcuPA, the fibrinolytic action mediated by the latter is substantially enhanced. Therefore, it is evident that suPAR stimulates tcuPA mediated fibrinolysis.

Distribution of Micro-emboli

Freshly prepared micro-emboli (15–30,000 cpm/0.2 ml) were re-suspended and injected into the tail vein of mice. At 10 min, 1, 3, and 5 hr post-injection, the mice were anesthetized with metophane and 0.1 ml of blood were withdrawn from them into a heparinized capillary tube by retro-orbital puncture. The mice were then sacrificed by cervical dislocation and their major organs were immediately harvested, rinsed in saline, dried on filter paper and weighed. The radioactivity level in each tissue was determined from which the exact dose (cpm) injected into each animal was calculated by subtracting the residual radioactivity in the tube and syringe after the injection, from the original amount.

The radioactivity associated with the tail of each mouse was determined in order to verify that injection into the vein was complete. Pilot studies indicated that >50% of the total injected dose of microemboli were distributed in a homologous pattern throughout the lung on autoradiography and light microscopy. In contrast, <5% of $^{125}$I-fibrinogen were found in association with the lungs.

Lysis of Pulmonary Micro-emboli uPA$^{-/-}$ mice and their syngeneic wild type littermates were anesthetized by intraperitoneal injection on Nembutal. The jugular vein was then cannulated using a siliconized polyethylene tube and PBS or tcuPA (alone, with soluble suPAR or with a combination of tcuPA/suPAR) were infused (IV infusion) via a PHD 2000 multi-syringe pump at a rate of 0.5 mg/kg/hr or 0.25 mg/kg/h, for 60 min. Five minutes after the onset of the infusion, $^{125}$I-micro-emboli were injected into the tail's vein, during which the mice remained anesthetized. At the end of the infusion, the mice were sacrificed, the tissues were collected and their radioactivity was determined as described above.

Results

FIG. 3. shows that while uPA$^{-/-}$ mice have impaired lysis of pulmonary micro-emboli compared to that with syngeneic wild type mice, in the presence of tcuPA lysis was enhanced and in the presence of tcuPA/suPAR the rate of lysis of such pulmonary micro-emboli was substantially elevated. This finding clearly teaches the stimulatory effect of suPAR on the thrombolytic activity of tcuPA.

What is claimed is:

1. A complex comprising tcuPA and suPAR in a proportion in favor of suPAR, said SuPAR:tcuPA complex being in the ratio of 10:1, and having fibrinolytic activity that is mediated by tcuPA under physiological conditions.

2. The complex as claimed in claim 1, wherein said fibrinolytic activity is specific to substantially fresh clots.

3. A pharmaceutical composition comprising an effective amount of the complex suPAR/tcuPA in the ratio of 10:1, said complex having an effective amount of suPAR to stimulate fibrinolytic activity mediated by an effective amount of tcuPA.

4. The pharmaceutical composition as claimed in claim 3, further comprising pharmaceutically acceptable carriers, diluents, adjuvants and preserving agents.

5. The pharmaceutical composition as claimed in claim 4, said composition, administered in an affective amount of the treatment of thrombotic events associated with the formation of fibrin clots.

6. The pharmaceutical composition as claimed in claim 5, wherein said thrombotic events include acute myocardial infarction, stroke, pulmonary emboli, cerebro- vascular events, disseminated intravascular coagulation (DIC) or deep vein thrombosis.

7. The pharmaceutical composition as claimed in claim 3, said composition being formulated in a dosage unit form.

* * * * *